United States Patent
Paulasaari et al.

(10) Patent No.: US 10,435,420 B2
(45) Date of Patent: Oct. 8, 2019

(54) HIGH-RI SILOXANE MONOMERS, THEIR POLYMERIZATION AND USE

(71) Applicant: Inkron Oy, Espoo (FI)

(72) Inventors: Jyri Paulasaari, Espoo (FI); Juha Rantala, Espoo (FI)

(73) Assignee: Inkron Oy, Espoo (FI)

( * ) Notice: Subject to any disclaimer, the term of this patent is extended or adjusted under 35 U.S.C. 154(b) by 0 days.

(21) Appl. No.: 15/559,436

(22) PCT Filed: Mar. 21, 2016

(86) PCT No.: PCT/FI2016/050173
§ 371 (c)(1),
(2) Date: Sep. 19, 2017

(87) PCT Pub. No.: WO2016/151192
PCT Pub. Date: Sep. 29, 2016

(65) Prior Publication Data
US 2018/0079761 A1 Mar. 22, 2018

Related U.S. Application Data

(60) Provisional application No. 62/135,723, filed on Mar. 20, 2015.

(30) Foreign Application Priority Data

Mar. 20, 2015 (FI) ..................... 20155194

(51) Int. Cl.
| | | |
|---|---|---|
| C08L 83/00 | (2006.01) | |
| C07F 7/08 | (2006.01) | |
| C07F 7/18 | (2006.01) | |
| C08G 77/12 | (2006.01) | |
| C08G 77/20 | (2006.01) | |
| C08L 83/06 | (2006.01) | |
| C08G 77/00 | (2006.01) | |
| H01L 33/56 | (2010.01) | |
| C09D 183/08 | (2006.01) | |
| H01L 23/29 | (2006.01) | |
| C08K 5/56 | (2006.01) | |

(52) U.S. Cl.
CPC .......... *C07F 7/0836* (2013.01); *C07F 7/1804* (2013.01); *C08G 77/12* (2013.01); *C08G 77/20* (2013.01); *C08G 77/80* (2013.01); *C08K 5/56* (2013.01); *C08L 83/00* (2013.01); *C08L 83/06* (2013.01); *C09D 183/08* (2013.01); *H01L 23/296* (2013.01); *H01L 33/56* (2013.01)

(58) Field of Classification Search
None
See application file for complete search history.

(56) References Cited

U.S. PATENT DOCUMENTS

| | | | | |
|---|---|---|---|---|
| 2,258,221 A | * | 10/1941 | Rochow ............... | C08G 77/14 174/110 S |
| 2,813,887 A | * | 11/1957 | Ramsden .............. | C07F 7/122 260/665 G |
| 3,114,759 A | * | 12/1963 | Lewis .................. | C07F 7/0852 252/78.3 |
| 3,385,878 A | | 5/1968 | Wu | |
| 4,278,784 A | | 7/1981 | Wong | |
| 4,756,971 A | * | 7/1988 | Virtanen .............. | B01J 20/286 210/656 |
| 6,492,204 B1 | | 12/2002 | Jacobs | |
| 6,806,509 B2 | | 10/2004 | Yoshino et al. | |
| 7,956,125 B2 | * | 6/2011 | Conner ................ | C07F 7/184 252/182.3 |
| 8,029,904 B2 | * | 10/2011 | Mosley ................ | C08G 77/28 427/77 |
| 2009/0146324 A1 | | 6/2009 | Auld et al. | |
| 2010/0233632 A1 | * | 9/2010 | Kawazu ............... | C08G 77/04 430/323 |
| 2013/0045292 A1 | | 2/2013 | Zhou et al. | |
| 2013/0045552 A1 | | 2/2013 | Lyons et al. | |
| 2014/0030660 A1 | * | 1/2014 | Takanashi ............ | G03F 7/11 430/323 |

FOREIGN PATENT DOCUMENTS

| | | |
|---|---|---|
| SU | 279055 | 8/1970 |
| SU | 427943 A1 | 5/1974 |

OTHER PUBLICATIONS

Jiajia N. et al.: An Efficient Ullmann-Type C—O Bond Formation Catalyzed by an Air-Stable Copper(I)-Bipyridyl Complex. Journal of Organic Chemistry, vol. 73 (19), 2008, pp. 7814-7817.
XP002758887, Sobolev et al: Synthesis of organosilicon monomers containing radicals with ether bonds. Zhurnal Obshchei Khimii vol. 39(12), pp. 2691-2694, 1969; Novel Chemical Solutions—Catalogue, Aug. 7, 2013.

* cited by examiner

*Primary Examiner* — Robert S Loewe
(74) *Attorney, Agent, or Firm* — Seppo Laine Oy

(57) ABSTRACT

Phenoxyphenylsilane monomers were synthesized and polymerized. The polymers have high refractive indices and excellent UV and thermal stability. Their water and oxygen permeability is lower than commercial phenyl silicone elastomers. They show good compatibility with metal oxide nanoparticles. The polymers of the invention are suitable as LED encapsulant, as light guide material in CMOS image sensors, in OLED devices, lasers and in other optical applications.

13 Claims, 1 Drawing Sheet

HIGH-RI SILOXANE MONOMERS, THEIR POLYMERIZATION AND USE

TECHNICAL FIELD

The present invention relates to silane monomers. In particular the present invention relates to high-RI siloxane monomers, to methods of synthesizing such monomers and to polymerization of the monomers to produce polymer of high refractive indices and excellent stability properties and good water and oxygen barrier.

BACKGROUND ART

Lighting industry is rapidly moving to LED-lighting systems. Efficiency and power output of a typical LED has risen quickly. Epoxides have traditionally been used as an encapsulant but the conventional materials can no longer handle the intense light flux and heat that state-of-the-art LEDs generate. Dimethylsilicone (PDMS), a known encapsulating material for electronic devices, has recently been used more and more as an encapsulant for LEDs due to better durability and resistance to yellowing than epoxides.

As far as the use of dimethylsilicone is concerned reference is made to U.S. Pat. Nos. 4,278,784, 6,492,204 and 6,806,509.

However, PDMS has a relatively low refractive index (RI ~1.4) compared to LED-chip ('epi', e.g. InGaN, RI~2.5) and many phosphor materials used in white LEDs (for example yttrium aluminium garnet, 'YAG', RI~1.85). This refractive index mismatch creates internal reflections, which lower the light output and efficiency of the device. Replacing PDMS with higher RI phenyl silicones (RI~1.50 . . . 1.55) somewhat improves the situation but there is still a need for even higher RI materials that can withstand the conditions inside LEDs without yellowing and are suitable for LED manufacturing.

SUMMARY OF INVENTION

Technical Problem

It is an aim of the present invention to remove at least a part of the problems relating to the known solutions and to provide a novel polymeric material which has high refractive index and excellent stability properties.

It is another aim of the present invention to provide novel monomers.

It is a third aim of the present invention to provide methods of producing polymers from the monomers.

It is a fourth aim of the present invention to provide the use of the novel polymeric materials.

Solution to Problem

In connection with the present invention, it has surprisingly been found that phenoxyphenylsilanes and bis-phenoxyphenylsilanes are excellent monomers for polymers suitable for use, for example, as LED encapsulants.

The present invention provides a siloxane monomer having the formula $$(p\text{-Ph-O-Ph})_2\text{Si}(X)_2 \quad\quad\quad \text{I}$$

wherein
each X is a polymerizable group independently selected from hydrogen, lower alkoxy optionally containing an alkoxy substituent, halo, hydroxy or —OSiMe$_3$.

The present invention also provides siloxane monomers having the formula $$p\text{-(PhO)}_y\text{Ph-Si}(X)_3 \quad\quad\quad \text{II}$$

wherein
each X is a polymerizable group independently selected from hydrogen, lower alkoxy optionally containing an alkoxy substituent, halo, hydroxy or —OSiMe$_3$, and y is 1 or 2.

The polymers derived from phenoxyphenylsilane and/or bis-phenoxyphenylsilanes

Polymers obtained from the monomers are characterized by what is stated in the characterized part of claim 6.

Advantageous Effects of Invention

The present monomers are di- or triphenyl ether silanes.

Considerable advantages are obtainable by the present invention. Thus many of the polymers derived from phenoxyphenylsilane and/or bis-phenoxyphenylsilanes, for example by conventional hydrolysation and polymerization procedures, have refractive indices higher than phenylsiloxanes or phenylsilicones. These polymers are resistant to UV-A and blue light and have high thermal stability. Typically, a polymer of the present kind has Oxygen Transmission Rate (OTR) and Water Vapor Transmission Rate (WVTR) less than 50% of OTR and WVTR of phenylsilicone elastomers.

Next, embodiments of the present technology will be described in more detail.

EMBODIMENTS

Figure 1:
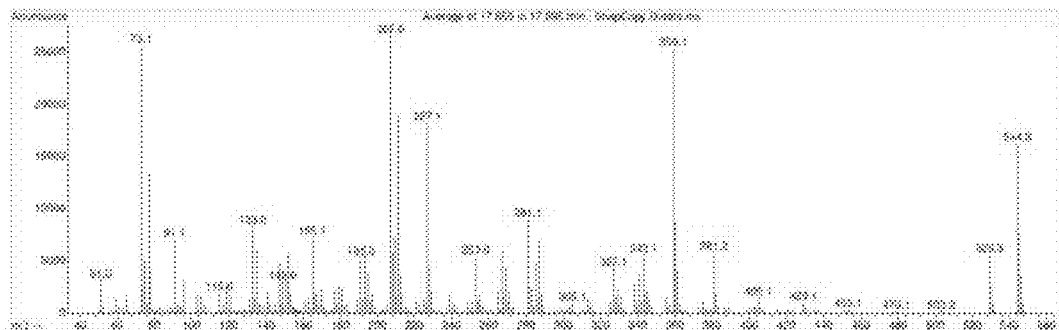
FIG. 1 shows the Mass Spectrum of bis(phenoxyphenyl)-bis(trimethylsiloxy)silane.

A first embodiment comprises a siloxane monomer A having the formula $$(p\text{-Ph-O-Ph})_2\text{Si}(X)_2 \quad\quad\quad \text{I}$$

wherein
each X is a hydrolysable group independently selected from hydrogen, lower alkoxy optionally containing an alkoxy substituent, halo, acetoxy, hydroxy or —OSiMe$_3$.

A second embodiment comprises a siloxane monomer B having the formula $$p\text{-PhOPh-Si}(X)_3 \quad\quad\quad \text{IIa}$$

wherein
each X is a hydrolysable group independently selected from hydrogen, and lower alkoxy optionally containing an alkoxy substituent, halo, acetoxy, hydroxy or —OSiMe$_3$.

A third embodiment comprises a siloxane monomer C having the formula $$p\text{-PhOPhOPh-Si}(X)_3 \quad\quad\quad \text{IIb}$$

wherein
each X is a hydrolysable group independently selected from hydrogen, and lower alkoxy optionally containing an alkoxy substituent, halo, acetoxy, hydroxy or —OSiMe$_3$.

In a general embodiment, siloxane monomer C meets the general formula (IIc):

PhOPhOPh-Si(X)$_{4-k}$     IIc wherein each X is a hydrolysable group independently selected from hydrogen, and lower alkoxy optionally containing an alkoxy substituent, halo, acetoxy, hydroxy or —OSiMe$_3$.
and k is an integer 1 to 3.

An embodiment of formula IIc has the formula p-PhOPhOPh-Si(X)$_{4-k}$, wherein X and k have the same meaning as above.

Preferably, in the meaning of X, lower alkoxy stands for an alkoxy group having 1 to 6 carbon atoms, in particular 1 to 4 carbon atoms. Examples of such alkoxy groups include methoxy (—OMe), ethoxy (—OEt), n- and i-propoxy (—OPr), n-, i- and t-butoxy (—OBu). Further examples include alkoxyethers, such as —O—CH$_2$CH$_2$—O—CH$_3$.

In the meaning of halo, X preferably stands for chloro (Cl) or bromo (Br).

Specific examples of monomers according to the above formulas are
bis(phenoxyphenyl)-dimethoxysilane;
bis(phenoxyphenyl)-dihydroxysilane;
bis(phenoxyphenyl)-bis(trimethylsiloxy)silane;
p-phenoxyphenyltrihydroxysilane; and
p-phenoxyphenoxyphenyltrimethoxysilane The present monomers are phenyl ether silanes which do not contain any non-hydrolysable groups bonded to the silane, such as phenyl groups.

The monomers are conveniently prepared by Grignard synthesis, using tetra-alkoxysilane as starting monomer and bromophenyl phenyl ether or bromophenyl phenyl phenyl diether as the organohalide.

The starting silane can also be methyltrialkoxysilane or vinyltrialkoxy silane if extra functionality is needed. For example, vinyltrimethoxysilane can be used for crosslinking via vinyl group by radical or hydrosilylation curing mechanism. Chlorosilanes such as dichlorosilane can also be used for Grignard synthesis of phenoxyphenylsilane or phenoxyphenoxyphenylsilane monomers.

In an embodiment, a monomer of either formulas I or II can be polymerized by conventional hydrolysis polymerization. Thus a monomer of formula I or any of formulas IIa to IIc can be homopolymerized or it can be copolymerized with a monomer of the other formula (IIa to IIc or I).

Thus, in one embodiment, a polymer is obtained by hydrolysis and polymerization of a monomer of formula IIb or IIc optionally with one or two or three monomers selected from siloxane monomers having formulas I, IIa or IIc or IIb, respectively.

It is also possible to prepare a copolymer with either of monomers of formula I or II with another monomer selected from the group of silane, germane and zirconium alkoxide and combinations thereof. Thus, terpolymers can also be produced.

The combined mol % of moieties obtained from monomers of formulas I and IIa to IIc used in the polymer synthesis is at least 10 mol % of the total monomer amount.

In embodiments, basic or acidic catalysts are used.

In one embodiment, before the condensation reaction, some or all alkoxy groups are hydrolyzed to silanol groups. Base catalysis favors the reaction between alkoxy group and silanol group, and this property can be used to ensure successful co-polymerization reaction between different silane monomers. Base catalysis is also favored, if acid-sensitive functional groups such as vinyl ethers are present.

For example, bis(p-phenoxyphenyl)dimethoxysilane (Bis(PhOPh)DMOS) can be hydrolyzed with dilute HCl, to yield bis(p-phenoxyphenyl)dihydroxysilane, which can be isolated and stored because of the relatively good general storage stability of bisarylsilanediols.

Then, it can be polymerized with, for example methacryloxymethyltrimethoxysilane (MAMTMOS) using alkaline metal hydroxides such as LiOH, NaOH, KOH, Ba(OH)$_2$ or their alkoxides such as NaOMe, ammonia, amines, various phosphazene super bases, guanidines or tetraalkylammonium hydroxides such as tetrapropylammonium hydroxide.

The hetero condensation by-product is methanol, and silanol-silanol homo condensation reaction is often just a small side reaction. Base catalysis is thus favored, if monomers with high differences in their general reactivities are polymerized.

Acid catalyzed polymerization of alkoxysilane (or silylhalides or acyloxysilanes) is accomplished by using dilute acid solutions to both hydrolyze and polymerize silane monomers simultaneously. However, hydrolyzation and polymerization can also sometimes be done separately. Acid catalysis is favored polymerization method if base-sensitive functional groups are present, which one does not want to react during polymerization (such as Si—H or some ester-linkages). Often, dilute mineral acids such as d.HCl, d.H$_2$SO$_4$ or d.HNO$_3$ are used. Also carboxylic acids such as acetic acid or oxalic acid can be used. Various phosphonitrilic chlorides are also found to be excellent silanol condensation catalysts. Lastly, some weakly acidic salts can also promote silanol condensation, such as pyridinium hydrochloride.

The concentration of the dilute acids is typically 0.001 M to 1 M, in particular from 0.01 to 0.5 M.

Generally in any of the above copolymers, the combined mole % of monomer A (monomer of formula I) and monomer B (monomers of formulas IIa to IIc) in the polymer synthesis is at least 10 mol % of the total monomer amount, preferably at least 20 mole %, for example at least 30 mole %, at least 40 mole %, at least 50 mole %, at least 60 mole %, at least 70 mole %, at least 80 mole % or at least 90 mole %.

Polymerization can be carried out at increased temperature optionally in the presence of added catalysts (0.0001 to 5 mole %, for example 0.001 to 2.5 mole %, calculated from the total molar amounts of monomers and catalysts).

In the presence of added catalysts, the polymerization is typically carried out at low or moderate temperatures from about 10 to 200° C., for example 20 to 180° C., or 30 to 170° C., or 40 to 150° C.

Typically, in the absence of an added catalyst, the temperature is in the range of 200 to 500° C., for example 200 to 400° C., for instance 200 to 350° C. In particular, without condensation catalysts temperatures between 200 . . . 400° C. are usually required.

In addition to the basic or acidic catalysts discussed above, the catalysts employed can be selected from the group of zirconium alkoxide and titanium alkoxide catalysts.

In one embodiment, hydrolyzation and polymerization is carried out in the presence of water.

In one embodiment, hydrolyzation and polymerization is carried out in the absence of water.

Solvents such as acetone, isopropanol, toluene, or methanol can be used to get the components into a single phase or to facilitate proper stirring.

Anhydrous polymerization can be also used to form siloxane polymers. For example, reaction between alkoxysilanes and acyloxysilanes creates siloxane polymers and is catalyzed by titanium or zirconium alkoxides. The condensation co-product is an ester, for example methyl acetate in case of methoxysilane and acetoxysilane.

The fourth reaction that can be used to polymerize the silane monomer of the invention is acid or base catalyzed ring opening polymerization of cyclic siloxanes. e.g. bis (phenoxyphenyl)-dimethoxysilane (Bis(PhOPh)DMOS) can be hydrolyzed and condensed into cyclic trimers, tetramers or pentamers, that can undergo ring opening in right conditions to yield linear polymer. Other cyclic silanes can be copolymerized along with cyclic bis(phenoxypheny)siloxanes.

The polymer can be essentially linear or it can contain one or more monomers providing side groups to the main chain. Molecular weight can vary between 500 . . . 1,000,000 g/mol, more preferably between 500 . . . 10,000 g/mol.

In one embodiment, the polymer chains are crosslinked by crosslinkable groups of at least one species selected from the group of Si—OH, Si—OMe, Si—OEt, Si—H, vinyl, acryl, methacryl, epoxy, acetoxy and mercapto groups.

One aim of crosslinking is to set the material so that it no longer flows. Some crosslinking systems are one component, others are two component. For example, peroxide curing is one component system, while platinum-curable compositions consist of two components, the first having Si-vinyl-containing polymer and platinum, eg. platinum-divinyltetramethyldisiloxane complex (Karstedt's catalyst) plus optional inhibitor such as ETCH (1-ethynylcyclohexanol) and phosphines, and the second component having siloxane polymer with Si—H functional groups. Furthermore, siloxane resins can sometimes be thermally cured even in the absence of any specific crosslinking groups using just heat to crosslink residual silanol groups.

In one embodiment, a polymer obtained by any of the above embodiments, exhibits an Oxygen Transmission Rate (OTR) and a Water Vapor Transmission Rate (WVTR) which is less than 50% of the corresponding OTR and WVTR values of phenylsilicone elastomers.

In one embodiment, polymer composites are provided. The composites are in particularly provided from a polymer according to any of the embodiments disclosed above in combination with metal, silicon oxide, or diamond, in the shape of particles, flakes, nanoparticles or nanorods.

In one embodiment, the polymer can also be blended with fumed silica, carbon black, metal oxides such as $ZrO_2$, $TiO_2$, $Ta_2O_5$, $Al_2O_3$, silver particles, nano diamonds, gold nanorods, glass fibers, color inks or other polymers, in order to tailor specific properties of the polymer system. For example titanium oxide and zirconium oxide nanoparticles can be used to further increase the refractive index of the polymer.

In one embodiment, depending on the curing system and intended application, thermo acid generators, thermo base generators, radical initiators, noble metal catalysts such as platinum, light induced radical, base or acid generators, tin-catalysts and titanium alkoxides can be added to facilitate polymer crosslinking.

Also, commercial heat and light stabilizers such as hindered amines, phosphines, phenolic stabilizers can be incorporated to further enhance those properties.

Generally, the amount of added components in the polymer composites of any of the above embodiments, is typically 0.1 to 75 wt %, typically 1 to 50 wt %, for example 2.5 to 40 wt %, or 5 to 30 wt %, of the total weight of the polymer composite.

The polymers and the polymer composites can be used for producing films. Typically such films have thicknesses in the range of 0.01 um to 3 mm, for example 0.05 to 500 um.

A film made of a polymer or a polymer composite of the above embodiments can be produced by a technique selected from the group of spin-on, spraying, dip-coating, slit-coating or screen-printing the polymer, followed by optional drying and curing by moisture, heat or UV.

The polymers or polymer composite, optionally in the form a films, can be employed in the following applications, to mention a few:
LED-devices,
CMOS-image sensors,
LCD-displays and OLED-devices, and
optical applications.

EXAMPLES

Example 1

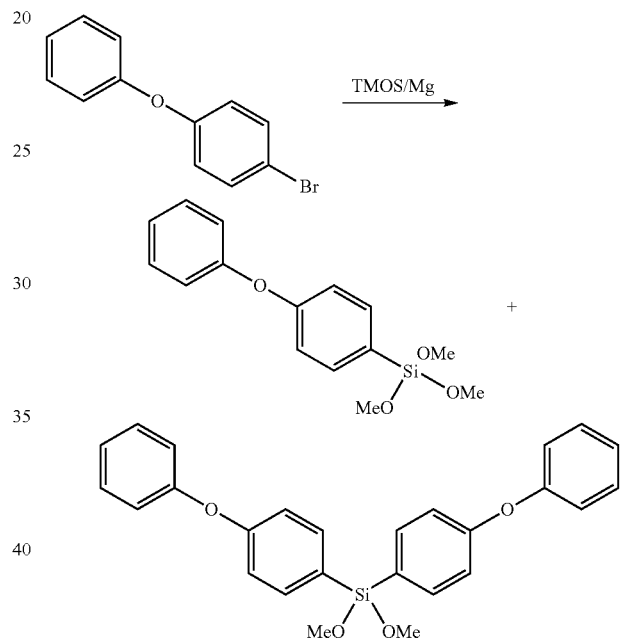

THF (150 g), magnesium (26 g), tetramethoxysilane (150 g) were placed in a 1 L three-neck flask under dry nitrogen, and heated to reflux. Para-bromophenyl ether was slowly dripped in. More THF (~200 mL) was gradually added to facilitate magnetic stirring. When the reaction was over, judged by GC/MS, heptane was added to precipitate magnesium salts. After filtration, solvents were removed in rotary evaporator. Distillation of the crude product gave two fractions (PhOPh)Si(OMe)$_3$, bp 120° C./0.1 mbar and Bis (PhOPh)Si(OMe)$_2$, bp 220° C./0.1 mbar.

Example 2a

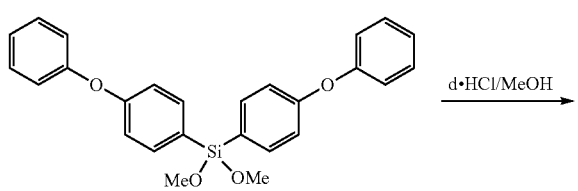

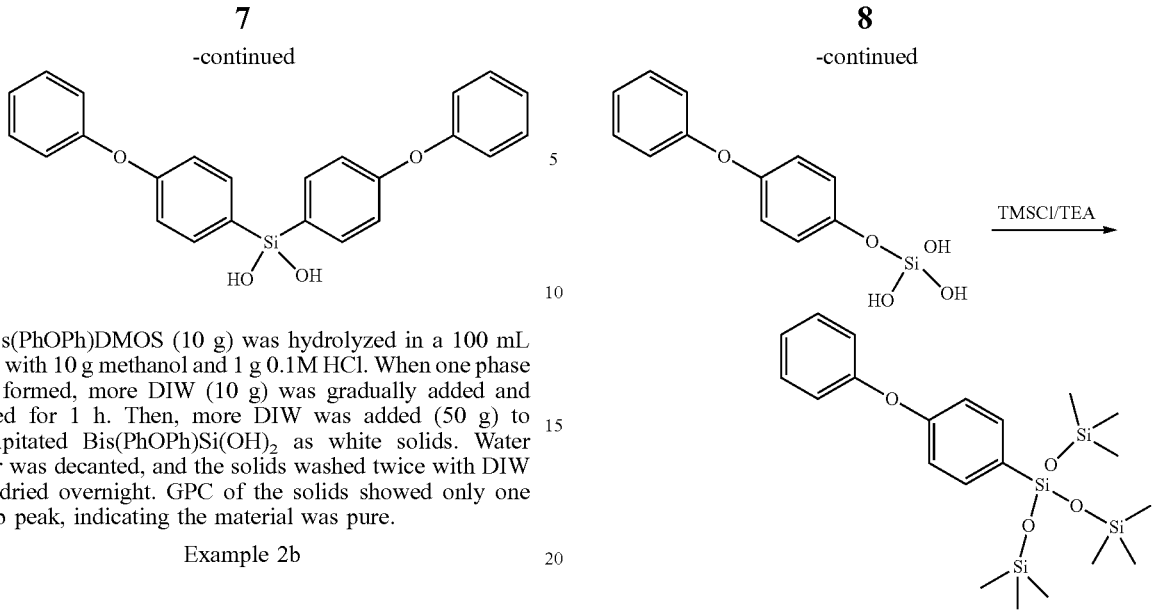

Bis(PhOPh)DMOS (10 g) was hydrolyzed in a 100 mL flask with 10 g methanol and 1 g 0.1M HCl. When one phase was formed, more DIW (10 g) was gradually added and stirred for 1 h. Then, more DIW was added (50 g) to precipitated Bis(PhOPh)Si(OH)$_2$ as white solids. Water layer was decanted, and the solids washed twice with DIW and dried overnight. GPC of the solids showed only one sharp peak, indicating the material was pure.

Example 2b

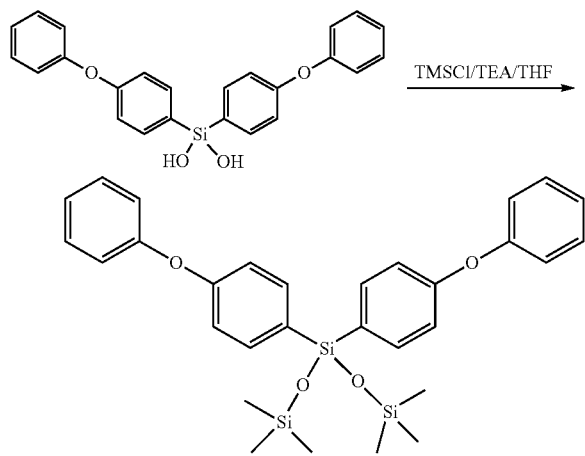

Bis(PhOPh)Si(OH)$_2$ (0.1 g) was dissolved in dry THF in a 8 mL glass vial, and triethylamine (1 mL) and trimethylchlorosilane (1 mL) were quickly added in. The vial was shaken for two minutes and the TEA-salts were removed by filtration. GPC and GC/MS of the sample (FIG.) showed a peak at m/z=544, that corresponds to expected bis(phenoxyphenyl)-bis(trimethylsiloxy)silane. It has molecular weight of 544.85.

The MS-spectrum bis(phenoxyphenyl)-bis(trimethylsiloxy)silane is shown in FIG. 1.

Example 3

PhOPhSi(OH)$_3$

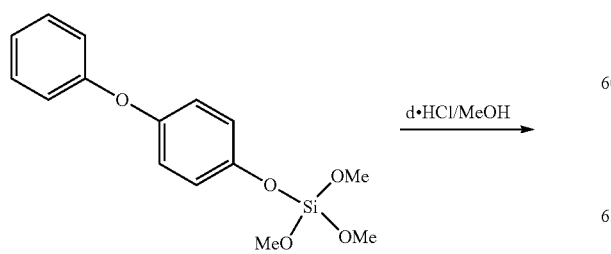

PhOPhTMOS (20 g) from Example 1 was diluted with methanol (20 g). 0.1M HCl (1 g) was added, followed by slow addition of DIW (100 g). White powderous precipitate was formed. It was filtered, washed with DIW and dried under vacuum at 35° C. for two hours. Small sample (0.1 g) of the powder was dissolved in THF (1 mL), and TMS-silylated by quickly adding it to a solution of MTBE (4 mL), trimethylchlorosilane (TMSCL, 1 mL) and dry triethylamine (1.5 mL). GC/MS of the sample gave one peak at m/z=464 (FIG.), corresponding to tris(trimethylsiloxy)-phenoxyphenylsilane. This shows, that the white powder was p-phenoxyphenyltrihydroxysilane, PhOPhSi(OH)$_3$. It has molecular weight of 464.85.

Figure 2:
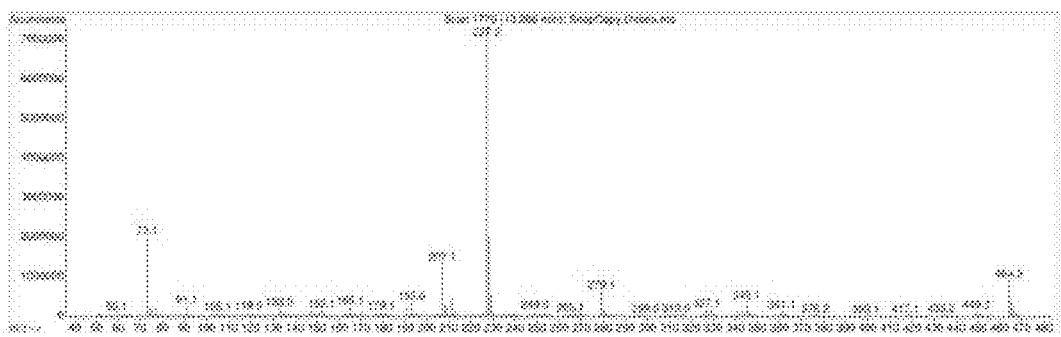
FIG. 2 shows the Mass Spectrum of tris(trimethylsiloxy)-phenoxyphenylsilane.

The MS-spectrum tris(trimethylsiloxy)-phenoxyphenylsilane is shown in FIG. 2.

Example 4

PhOPhOPhTMOS

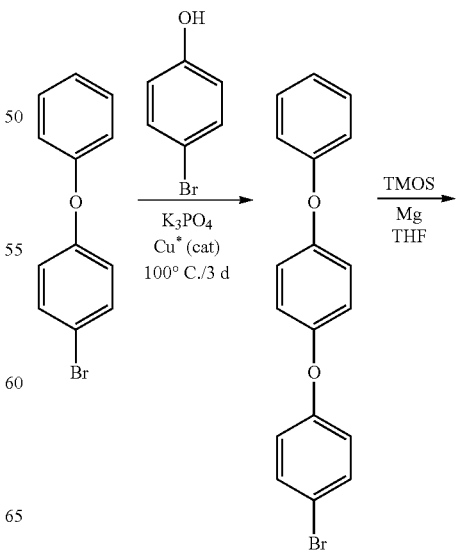

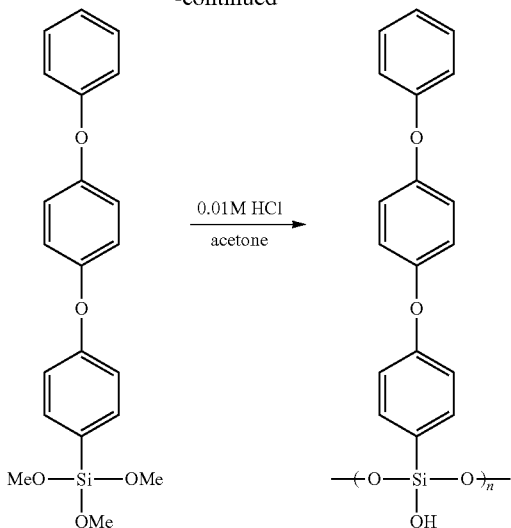

Para-bromophenyl phenyl ether (20 g), p-bromophenol (9 g), $K_3PO_4$ (17 g), $Cu(BiPy)_2BF_4$ (1 g, "Cu*", a soluble copper catalyst by N. Jiajia et. al., J. Org. Chem. 2008, 73, 7814-7817) and dimethylformamide (DMF, 60 mL) were placed in a 250 mL rb flask with a loose stop cock, and the system was heated and stirred for three days at 100° C. The solution was poured into water, and organics were dissolved in dichloromethane (DCM). After solvent evaporation and vacuum distillation (<1 mbar, 180° C.), seven grams of p-(phenoxyphenoxy)bromobenzene (PhOPhOPhBr) was obtained. It was further purified by recrystallization from MeOH, to yield pure white crystals. Six grams of PhOPhOPhBr was dissolved in dry THF (15 g), and magnesium turnings (1 g) and TMOS (5 g) were added. The system was refluxed for 2 hours during which the reaction took place. THF was then evaporated, and the product was washed in toluene/DIW.

After distillation at <1 mbar/~200° C., ~5 grams of phenoxyphenoxyphenyltrimethoxysilane (PhOPhOPhTMOS) was obtained in 95+% purity by GC/MS. The monomer was hydrolyzed and polymerized in acetone by dil. HCl to yield a mixture of both oligomers and polymer (Mw/Mn=2325/1924 by GPC), from which the polymer formed a colorless film by spin coating and curing at 250° C. The film had high refractive index (RI=1.612 at 633 nm).

Figure 3:
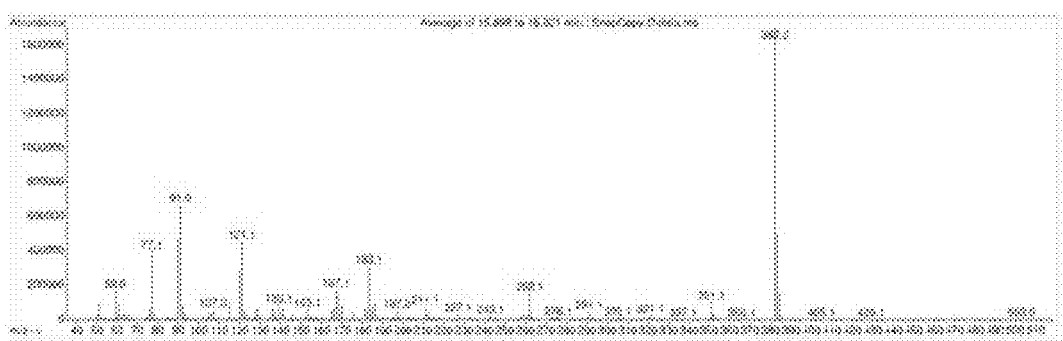
FIG. 3 shows the Mass Spectrum of PhOPhOPhTMOS.

The Mass spectrum of PhOPhOPhTMOS is shown in FIG. 3.

Polymer Example 1

PhOPhOPhTMOS (3 g) was hydrolyzed and polymerized in acetone (3 g) by dil. HCl (1 g) to yield a mixture of both oligomers and a polymer fraction (Mw/Mn=2325/1924 by GPC), from which the polymer formed a colorless film by spin coating and curing at 250° C. The film had high refractive index (RI=1.612 at 633 nm).

Polymer Example 2

All of the crude $Bis(PhOPh)Si(OH)_2$ from Example 2, PhOPhTMOS (5 g), methacryloxymethyltrimethoxysilane (2 g) and 0.2 g 5% $Ba(OH)_2$ in methanol were placed into the flask. The flask was heated to 80° C. while stirring for 1 hours. After cooling the reaction to room temperature, barium hydroxide was neutralized with excess HCl and washed neutral with DIW in DCM solution. Drying at 95° C./1 mbar gave 13.8 g polymer with $M_w/M_n$=1389/884 and refractive index of 1.60171. It was formulated with Ciba® Darocur® 1173 (2%), and cured under mercury lamp at 365 nm (6 J/cm^2, 30 sec). A flexible, colorless film was obtained.

Polymer Example 3

PhOPhTMOS (6.5 g) and 3-methacryloxypropyltrimethoxysilane (MAPTMOS, 4.5 g) were placed in 100 mL rb flask along with 0.5 mL $Ba(OH)_2$/methanol solution (5%). The flask was heated to 70° C., and $Bis(PhOPh)Si(OH)_2$ (10 g) and $PhOPhSi(OH)_3$ (2.15 g) were gradually added in while temperature was risen to 80° C. After 2 h reaction, the polymer was washed neutral in toluene with 0.1 MHI and DIW, and precipitated twice from methanol. After drying, a clear polymer with $M_w/M_n$=2147/1265 and RI=1.59408 was obtained. It was formulated with Ciba® Darocur® 1173 (2%), and cured under mercury lamp at 365 nm (6 J/cm^2, 30 sec). A flexible, colorless film was obtained.

Polymer Example 4

PhOPhTMOS (15 g) and Bis(PhOPh)DMOS (5 g) were placed in a 50 mL rb flask with 0.5 mL $Ba(OH)_2$/methanol solution (5%). The flask was heated to 85° C., and $Bis(PhOPh)Si(OH)_2$ (25 g) was gradually added in. Temperature was risen to 90° C. After a 1 h reaction, the polymer was washed neutral in toluene with 0.1 MHI and DIW, and precipitated twice from methanol. After drying, a clear polymer (42 g) with $M_w/M_n$=2325/1580 was obtained. The polymer was dissolved in acetone (80 g) and 5 drops of cHCl was added, followed by slow addition of DIW (~100 mL). This way, terminal Si—OMe groups were hydrolyzed to Si—OH groups.

The polymer ($M_w/M_n$=1483/916 by GPC) was separated, dried, and divided into two ~18 g parts "A" and "B". The "A" part was diluted with 30 mL THF, and 1,3-divinyltetramethyldisilazane (5 g) was added, along with small amount of perfluoroaniline-trifluoromethane sulfonate salt as a catalyst. The reaction was allowed to proceed for 24 h at room temperature. The part "B" was treated similarly, but using 1,1,3,3-tetramethyldisilazane as the silylating agent for Si—OH groups. The molecular weights of the two polymers were: A—$M_w/M_n$=1870/1348, B—$M_w/M_n$=1714/1164.

Both "A" and "B" were evaporated, diluted with toluene and washed several times with dilute HCl and DIW, followed by drying in rotary evaporator.

Curing: The "A" part was formulated with Karstedt platinum (2% xylene solution from Aldrich) as 20 ppm Pt. Equivalent amount of part "B" was blended with aforementioned mixture of Part A and platinum. It was cured as a 50 μm thick film in an oven 150° C./1 hour. The film had initial transparency of 98.5%, which was not changed under UV-A irradiation (8 mJ/cm², 2 weeks). Also, transparency was more than 95% after heating the film for 300 h at 190° C. Oxygen Transmission Rate (OTR) was measured 240 cc/m²/day (at 23° C.) for a film with thickness of 0.56 mm, and Water Vapor Transmission Rate (WVTR) 3.4 g/m²/day, 90% RT, 23° C. Thus, OTR for this material is ~3 times smaller than for commercial phenyl silicone elastomer (~1120, Tx 0.91 mm) and WVTR is ~3½ times smaller (~19, Tx 0.91 mm). This is important, since some phosphors which are mixed with LED-siloxane resin to give high-CRI (color rendering index) white light are moisture and oxygen sensitive. A thinner film of the mixture Part A+Part B was formed by spin casting it from 20% xylene solution, followed by baking at 150° C./1 hour. Colorless film with Tx~1 µm and RI ~1.61 at 633 nm was obtained, as measured by Woollam ellipsometer.

The 1:1 mix of Part A+Part B (total 0.5 g) was also formulated with $ZrO_2$-nanoparticles (2 g, 27% solution in MIBK (MZ-300B by Sumitomo), polymer:$ZrO_2$-np ~1:1). The solution was filtered through a 0.45µ PTFE filter and spin coated on a silicon wafer. After curing at 150° C. for 1 h, a clear, transparent 1.5 micron film was formed with RI=1.72. The film remained colorless several days in an oven at 190° C., indicating good thermal stability.

INDUSTRIAL APPLICABILITY

The polymers of the invention are suitable as LED encapsulant, as light guide material in CMOS image sensors, in OLED devices, lasers and in other optical applications.

CITATION LIST

Patent Literature

U.S. Pat. No. 4,278,784,
U.S. Pat. No. 6,492,204
U.S. Pat. No. 6,806,509
US 2009146324

Non-Patent Literature

N. Jiajia et. al., J. Org. Chem. 2008, 73, 7814-7817

The invention claimed is:

1. A polymer obtained by hydrolysis and polymerization of a first monomer with one or two second monomers, the first monomer having a formula:

p-PhOPhOPh-Si(X)$_3$      (IIb)

wherein each X is a hydrolysable group independently selected from the group consisting of hydrogen and an alkoxy group having 1 to 6 carbon atoms, the alkoxy group optionally containing a substituent selected from the group consisting of alkoxy, halo,hydroxy, acetoxy, and —OSiMe$_3$ and
the one or two second monomers having a formula:

(p-Ph-O-Ph)$_2$Si(X)$_2$      (I)

wherein each X is a hydrolysable group independently selected from the group consisting of hydrogen and an alkoxy group having 1 to 6 carbon atoms, the alkoxy group optionally containing a substituent selected from the group consisting of alkoxy, halo, acetoxy, hydroxy, and —OSiMe$_3$;
or p-PhOPh-Si(X)$_3$      (IIa)

wherein each X is a hydrolysable group independently selected from the group consisting of hydrogen and an alkoxy group having 1 to 6 carbon atoms, the alkoxy group optionally containing a substituent selected from the group consisting of alkoxy, halo, acetoxy, hydroxyl, and —OSiMe$_3$.

2. The polymer according to claim 1, further containing moieties of monomers selected from the group consisting of silane, germane and zirconium alkoxide and combinations thereof, the combined mol % of monomer according to formula I, IIa, and IIb, used in the polymer synthesis being at least 10 mol % of the total monomer amount.

3. The polymer of claim 1, obtained by polymerization in the presence of a catalyst, the catalyst selected from the group consisting of a basic catalyst, an acidic catalyst, zirconium alkoxide, and titanium alkoxide.

4. The polymer of claim 1, obtained by hydrolyzation and polymerization carried out in the presence of an increased temperature, optionally in the absence of added catalysts.

5. The polymer of claim 4, obtained by hydrolyzation and polymerization in the presence or absence of water.

6. The polymer of claim 1, cross-linked by cross-linkable groups of at least one species selected from the group consisting of Si—OH, Si—OMe, Si—OEt, Si—H, vinyl, acryl, methacryl, epoxy, acetoxy, and mercapto groups.

7. The polymer of claim 6, wherein the polymer comprises an Oxygen Transmission Rate (OTR) and a Water Vapor Transmission Rate (WVTR) less than 50% of the corresponding OTR and WVTR of phenylsilicone elastomers.

8. A polymer composite made from a polymer according to claim 1 in combination with a material selected from the group consisting of a metal, silicon oxide, metal oxide, or diamond, wherein the material comprises a member selected from the group consisting of particles, flakes, nanoparticles, and nanorods.

9. A film made of a polymer composite of claim 8 by spin-on, spraying, dip-coating, slit-coating or screen-printing the polymer, followed by optional drying and curing by moisture, heat or UV.

10. A film made of the polymer of claim 1 by spin-on, spraying, dip-coating, slit-coating or screen-printing the polymer, followed by optional drying and curing by moisture, heat or UV.

11. An LED-device comprising a film of the polymer of claim 1.

12. The LED-device of claim 11, wherein the film has a thickness of from 0.01 µm to 3.0 mm.

13. The LED-device of claim 12, wherein the film has a thickness of from 0.05 µm to 500 µm.

* * * * *